(12) United States Patent
Ponzini

(10) Patent No.: US 7,267,548 B2
(45) Date of Patent: Sep. 11, 2007

(54) SUPPORT FOR INTERDENTAL BRUSHES AND SIMILAR INSTRUMENTS FOR ORAL HYGIENE

(75) Inventor: Eligio Ponzini, Milan (IT)

(73) Assignee: Ponzini S.p.A., Lazzate (Milan) (IT)

( * ) Notice: Subject to any disclaimer, the term of this patent is extended or adjusted under 35 U.S.C. 154(b) by 0 days.

(21) Appl. No.: 10/493,429

(22) PCT Filed: Oct. 22, 2002

(86) PCT No.: PCT/EP02/11777

§ 371 (c)(1),
(2), (4) Date: Oct. 15, 2004

(87) PCT Pub. No.: WO03/034863

PCT Pub. Date: May 1, 2003

(65) Prior Publication Data

US 2005/0034257 A1 Feb. 17, 2005

(30) Foreign Application Priority Data

Oct. 25, 2001 (IT) .......................... MI2001A2245

(51) Int. Cl.
*A61C 3/00* (2006.01)

(52) U.S. Cl. .................. 433/141; 15/167.1; 132/321

(58) Field of Classification Search ............... 433/141, 433/146, 147, 216, 114, 126, 128, 129, 130, 433/39, 97, 99; 132/321; 403/285; 601/141; 15/106, 167.1, 172, 173, 176.3, 176.5, 176.6, 15/206

See application file for complete search history.

(56) References Cited

U.S. PATENT DOCUMENTS

| | | | | |
|---|---|---|---|---|
| 1,170,824 A | * | 2/1916 | Fernald | 62/413 |
| 1,379,880 A | * | 5/1921 | Seaborn | 433/130 |
| 4,030,199 A | * | 6/1977 | Russell | 433/147 |
| 4,222,143 A | | 9/1980 | Tarrson et al. | |
| 4,240,473 A | * | 12/1980 | Leonard | 141/91 |
| 4,731,896 A | * | 3/1988 | de La Tour | 15/106 |
| 4,780,923 A | * | 11/1988 | Schultheiss | 15/111 |
| 5,139,422 A | * | 8/1992 | Straihammer et al. | 433/126 |
| 5,293,661 A | * | 3/1994 | Appleby | 15/167.1 |
| 5,333,346 A | * | 8/1994 | Tarrson et al. | 15/167.1 |
| 5,342,284 A | * | 8/1994 | Lemon et al. | 601/141 |
| 5,394,584 A | * | 3/1995 | Breitschmid | 15/167.1 |
| 5,581,838 A | * | 12/1996 | Rocco | 15/110 |
| 5,758,382 A | * | 6/1998 | Maekawa et al. | 15/167.1 |
| 6,170,111 B1 | * | 1/2001 | Rueb et al. | 15/106 |

FOREIGN PATENT DOCUMENTS

| | | |
|---|---|---|
| CH | 672 723 | 12/1989 |
| EP | 0 326 677 | 8/1989 |
| EP | 1 075 806 | 2/2001 |

\* cited by examiner

*Primary Examiner*—Melba N. Bumgarner
*Assistant Examiner*—Jonathan Werner
(74) *Attorney, Agent, or Firm*—Young & Thompson

(57) ABSTRACT

The present invention relates to a supporting device for an interdental cleaning means, of the type comprising a handle and a tightening head for an elongated appendix portion of said cleaning means, said tightening head comprising a central body around which a complementary rotating bush is mounted, and wherein said bush and said central body have a common hole for hosting said appendix portion, which hole is substantially parallel and offset relative to the rotation axis of the bush.

15 Claims, 3 Drawing Sheets

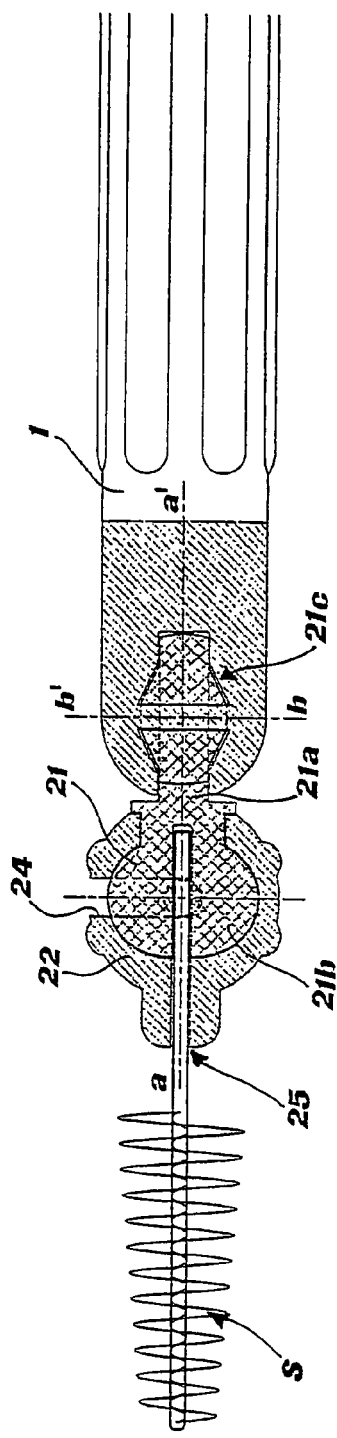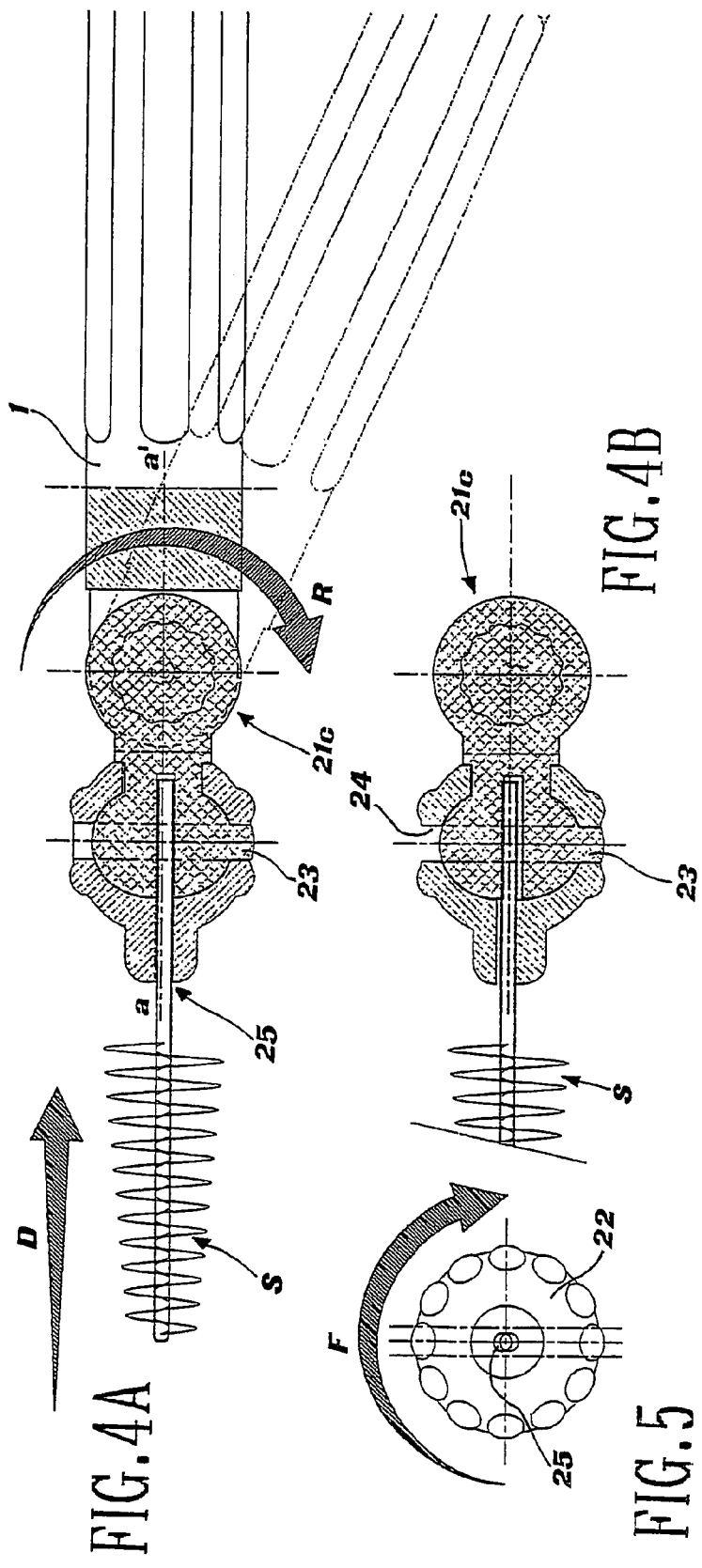
FIG.3  FIG.4A  FIG.4B  FIG.5

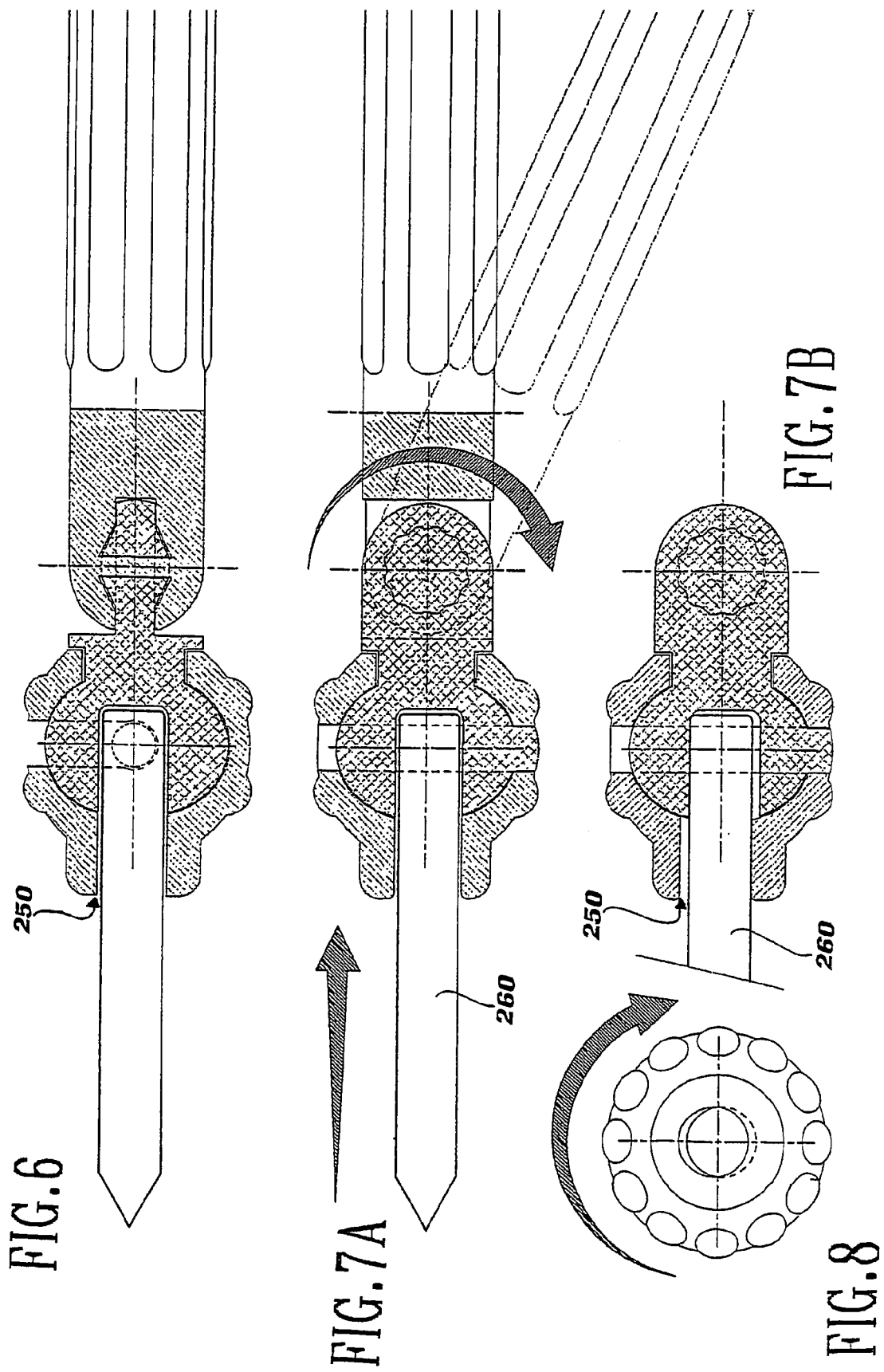

SUPPORT FOR INTERDENTAL BRUSHES AND SIMILAR INSTRUMENTS FOR ORAL HYGIENE

BACKGROUND OF THE INVENTION

The present invention relates to a supporting device for an interdental cleaning brush and the like.

DESCRIPTION OF THE RELATED ART

It is known that interdental cleaning brushes, which usually consist of a suitably shaped handle onto the free end of which a small disposable brushing body is mounted, are very diffused on the market.

Since it is suitable, for clear hygienic and practical reasons, that said small brushing body be frequently discarded and replaced with a new one, it is important that said body may be very easily and quickly engaged/disengaged with and from the shaped handle.

Known devices of this type are illustrated, for example, in U.S. Pat. No. 4,319,377, U.S. Pat. No. 4,222,143, EP 311, 937 and EP 537,663.

All of these devices are designed so that a wire brush provided with an appendix portion, usually made from a twisted double metal wire, is attached to the handle. Such devices exploit the high deformability of said appendix, which is inserted into a through hole and then bent by about 90° against the handle, where it is blocked by a tightening element.

This approach has various drawbacks, among which there are:

- the required 90° bending of the metal appendix portion of the brush results in great deformation of the material, which may reach and exceed the yielding point and this may prevent further uses of the brush—e.g. re-attaching the brush after having first wrongly attached it; at any rate, the appendix must be made of materials elastic enough to bear such deformation, which, so far, has restricted the choice exclusively to metal materials;
- the appendix portion, inserted into a through hole of the device, before being deformed and blocked, projects from the handle in a way that is dangerous for the user;
- the device is necessarily provided with a room for hosting the inserted bent appendix portion: this implies the existence of a recess, where dirt and bacteria may easily accumulate;
- finally, in order to bend the appendix portion and cover it completely, so that it does not remain exposed within the user's mouth, it is necessary that the (linear or angular) stroke of the moveable tightening element of the device be ample, which is not always easy to obtain, considered the very small size of said element.

SUMMARY OF THE INVENTION

The object of the present invention is to provide a supporting device for an interdental brush that eliminates the above-illustrated drawbacks, in particular through a tightening means that provides a secure block for the brush that also has a short angular stroke, that is able to hold appendix portions of various materials, that does not have any large, dirt-collecting recesses and that under no conditions allows the dangerous exposure of the pointed end of the appendix portion.

BRIEF DESCRIPTION OF THE DRAWINGS

Further advantages and features of the device according to the invention will however result from the following detailed description of some preferred embodiments, given by way of example and illustrated in the appended drawings, wherein:

FIG. 3 is a partially sectional view taken along the line III-III of FIG. 2;

FIG. 4A is a partially sectional view taken along line IV-IV of FIG. 1, in a loose condition of the brush;

FIG. 4B is a view as the one in FIG. 4A in a blocked condition of the brush;

FIG. 5 is a front elevation view of the tightening head; and

FIGS. 6, 7A, 7B and 8 are views corresponding to, respectively, the views of FIGS. 3, 4A, 4B and 5 concerning a second embodiment.

DESCRIPTION OF THE PREFERRED EMBODIMENTS

Figure 1:
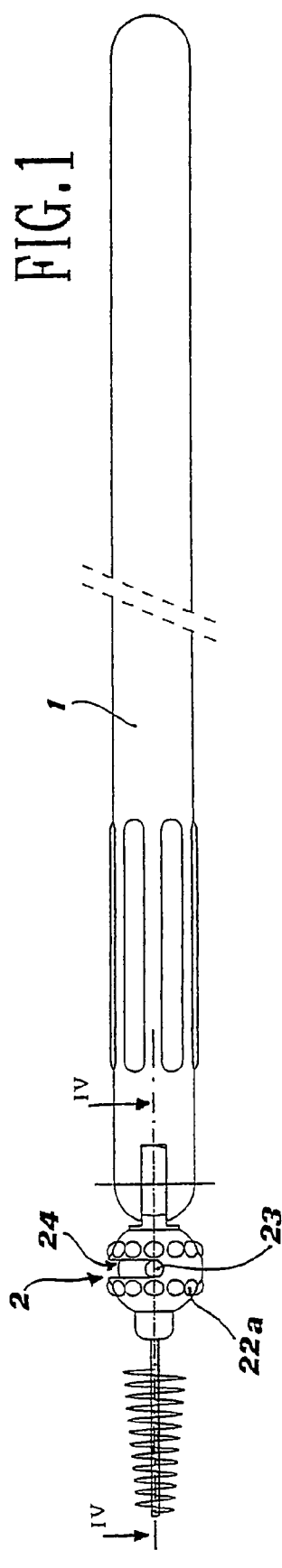
FIG. 1 is an interrupted plan top view of a first embodiment of the device according to the invention.
Figure 2:
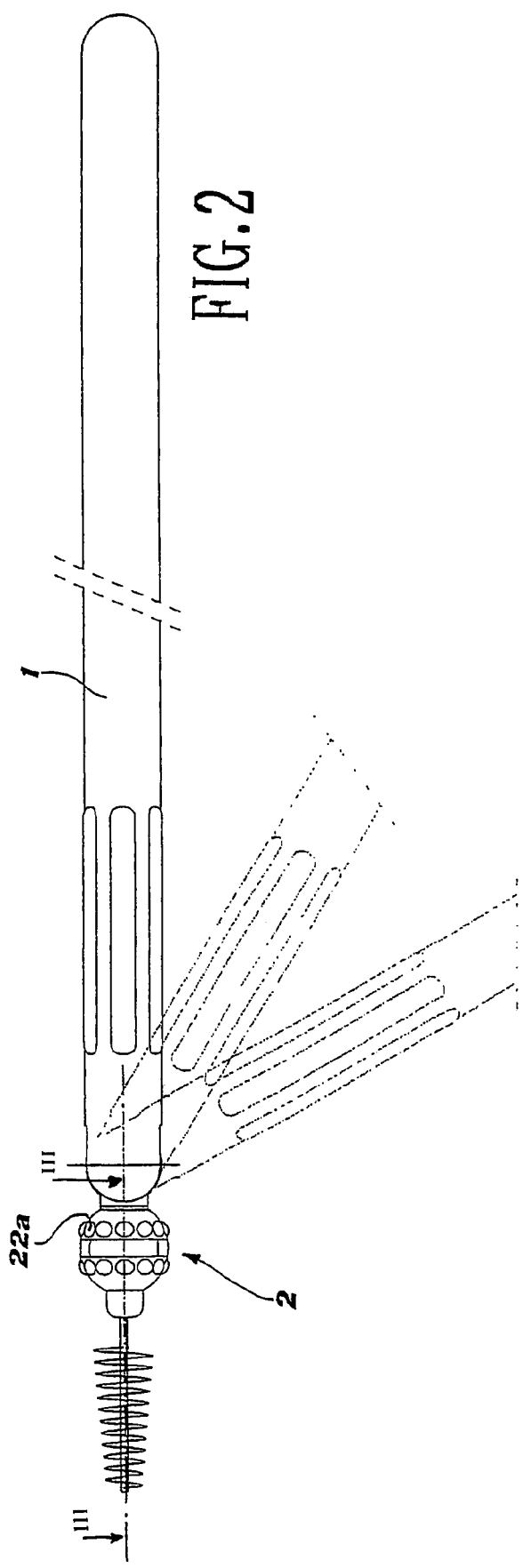
FIG. 2 is an interrupted side elevation view of the device in FIG. 1, wherein the two-positions of the handle, relative to the tightening head, are indicated by a thin line.

A supporting device for a brush is made, in a known manner, by a handle 1 onto the end of which a tightening head 2 is mounted, into which an interdental brush or similar instrument is removably attached.

According to the invention, the tightening head 2 comprises a central supporting body 21, attached to the handle 1, and a tightening bush 22 rotatably mounted onto the central body 21.

The central body 21 is composed of a stem 21a, through which it may engage the handle 1, and an axially symmetrical core 21b. Preferably, the core 21b is spherical and lightly depressed at the poles, as is well illustrated in the drawings.

The stem 21a is attached to the handle 1 through a hinged joint 21c, which allows to rotate and orientate the head 2 in the direction indicated by the arrow R. Advantageously, the hinge may be obtained by overmoulding the end of the handle 1 onto the hinge 21c, these two elements being of "incompatible" materials, therefore not weldable to each other during the overmoulding step.

The term "incompatible" must be understood as it is well described in EP 1075806, which is also in the name of the Applicant and shall also be considered included here as a reference.

In order to better guide the joint, the hinge 21c is shaped as a disc, the opposite bases of which being shaped like conical surfaces that are symmetrical relative to a rotation axis b-b'. In order to ensure a secure block, the hinge 21c is further provided with a central hole, coaxial with the rotation axis b-b', into which material of the handle 1 is apt to penetrate during the overmoulding process, which is going to become a pivoting pin.

On the opposite bases of the hinging disc 21c, low radial ribs are provided, which are designed to be inserted into corresponding grooves in the surrounding seat of the handle. The engagement of the ribs into the grooves ensures a stable angular positioning of the tightening head with respect to the handle, which may be modified by applying enough force to produce an elastic deformation of the ribs when moving from one groove to the next.

From the periphery of the core 21*b*, at its equator, a short guiding stud 23 projects, the role of which will be illustrated hereinafter.

The tightening bush 22 is hollow and has an internal surface perfectly complementary to the revolving surface of the body 21, thus having the same symmetry axis. The external surface may be differently shaped, for example with non-slip knurlings or studs 22*a*, apt to make the bush comfortably usable by a person's fingers.

The bush 22 is further provided with a groove 24 along a circumferential arc of about 180°, at its equator, wherein the stud 23 is designed to move.

With this exemplary embodiment, the free rotation between the tightening bush 22 and the body 21 is guided and limited by the stud 23 being engaged into the groove 24, according to what the arrow F illustrates in FIG. 5.

The rotation axis, in the embodiments illustrated in the drawings, coincides with the symmetry axis a-a' of the tightening head 2.

According to the invention, the body 21 and the bush 22 also have a common longitudinal blind hole 25, placed eccentrically relative to the rotation axis a-a', apt to host the appendix portion of a brush S. The eccentricity of the hole 25 may be determined depending on the diameter and on the material of which the brush appendix is made.

The hole 25 has a diameter that can quite loosely host the appendix part of the brush or other similar oral hygiene instrument. For example, the hole may have a diameter of 0,6 mm.

In an inoperative condition of the bush 22 and the body 21, the respective portions of the hole 25 are aligned with each other (FIGS. 3 and 4A), therefore it is possible to freely insert therein (arrow D) and withdraw therefrom the appendix portion of the brush S. In this inoperative or idle state, the bush 22 is completely rotated in one direction and the stud 23 abuts against an end-of-travel wall of the groove 24 (FIG. 1).

In an operative position of the bush 22 and the body 21-obtainable by rotating the bush 22 from the inoperative position, e.g. in the direction indicated by the arrow F—the respective portions of the hole 25 are out of axis relative to each other on a common plane (FIG. 4B). As can be argued, this results in a tightening of the appendix portion of the brush S, which gets deformed and remains therefore securely fixed into the tightening head 2.

The reaching of the operative tightened position is preferably indicated by an opposite end-of-travel wall of the groove 24, against which the stud 23 abuts, for example, after a 180° rotation.

In order to assure the user that he or she has definitely reached the end-of-travel, as well as to avoid any involuntary rotations of the bush 22, any known click-blocking system may be provided in the complete and secure tightened position of the brush.

For example, the groove 24 has a restriction near the end-of-travel, so that the user must put some effort to make the stud 23 pass behind the restriction. This way, the stud will stop at the end-of-travel and no accidental disengagement will be possible. Furthermore, the user will clearly perceive, due to the effort and to the snapping "click", when the instrument reaches a secure operative position.

According to another embodiment, illustrated in FIGS. 6-8, the bush 22 and the body 21 have an axial hole 250 with a larger diameter, for example 3 mm, to host a so-called "rubber point" 260, i.e. a small pin of a rubber material, to which abrasive material may be further added, having the function of an interdental instrument (such as a toothpick) or of a tooth-surface polishing instrument.

The tightening principle of the rubber point 260 is the same as the one illustrated above.

Obviously, such a hole 250, having a large diameter, is not apt to block the appendix portion of a brush, which is typically thinner.

According to a further embodiment of the invention (not illustrated), the device of FIGS. 6-8 is provided with a false rubber point, having the function of a tightening adapter, which may be added and sold to the public in the same package with which the whole device is sold. This adapter, made of easily deformable material (e.g. elastomeric material), is slightly longer than the blind hole 250 and has a tightening axial hole.

When use of a classical rubber point is desired, said adapter is extracted from the hole 250. On the contrary, when one wishes to use an interdental brush on the same device, it is possible to insert the appendix part of the brush onto the tightening hole of the adapter and then tighten the latter inside the hole 250, thus obtaining the simultaneous tightening of the adapter and of the brush.

It is however understood that the invention is not limited to the specific embodiments illustrated above, which only constitute non-limiting examples of the scope of the invention, but also many alternatives are possible, all within the reach of an expert in the field, without thereby departing from the scope of said invention.

The invention claimed is:

1. Supporting device for an interdental cleaning means, comprising:
    a handle; and
    a tightening head of an elongated appendix portion of an interdental cleaning brush,
    said tightening head comprising a central supporting body and a tightening bush rotatably mounted on the central body,
    the central body comprising i) a stem attached to the handle through a hinge joint that allows the tightening head to rotate with respect to the handle and ii) an axially symmetrical core,
    the bush being rotatably about the core,
    said bush having an internal surface complementary to a revolving surface of the core,
    the bush and the revolving surface of the core having the same symmetry axis and having the same rotation axis, the symmetry axis being coincident with the rotation axis, wherein,
    said bush and said revolving surface of the core comprise respective portions of a common hole for hosting said appendix portion, which hole extends in a first direction through said bush and said revolving surface and said hole is substantially parallel and offset with respect to the rotation axis of the bush, and
    in an inoperative condition of the bush the respective portions of the hole are aligned and extend in the first direction, and in an operative condition of the bush said respective portions each extend in the first direction and are non-aligned, out of the axis relative to each other so that the stem is retained by being clamped and deformed.

2. Device as in claim 1, wherein said bush has a groove along a circumferential arc and said central body correspondently has a guiding stud apt to slide into said groove during the rotation of said bush around the body.

3. Device as in claim 2), wherein said groove lies on a circumferential arc of about 90° to 270°, preferably of 180°.

4. Device as in claim 2), wherein safety blocking means are provided between said groove and said guiding stud.

5. Device as in claim 2, further comprising a deformable adapter, which may be inserted into said common hosting hole and provided with a longitudinal hole into which the appendix portion of said interdental cleaning brush may be inserted,
said tightening head is of an elongated appendix portion of said interdental cleaning brush.

6. Device as in claim 1, wherein said tightening head may be adjusted relative to the handle.

7. Device as in claim 6), wherein,
said handle is made of a mouldable material, and
said stem ends with the hinge joint, onto which hinge joint an end of said handle is attached by overmoulding the handle onto the hinge joint.

8. Device as in claim 7), wherein said hinge joint is formed by a disc the bases of which have conical surfaces that are symmetrical relative to the rotation axis between the tightening head and the handle.

9. Device as in claim 8), wherein said hinge joint has a hole in the area corresponding to the rotation axis, into which a plastic, mouldable material of said handle is apt to be inserted, said plastic material becoming a constraining and pivoting stud.

10. Device as in claim 7), wherein said hinge joint has reciprocally engaging means, apt to determine a series of fixed angular positions between the handle and the tightening head.

11. Device as in claim 10), wherein said reciprocally engaging means are deformable to allow a staggered rotation of the hinge.

12. Device as in claim 11, wherein said hinge joint has a hole in the area corresponding to the rotation axis, into which a plastic, mouldable material of said overmoulded handle is apt to be inserted, said plastic material becoming a constraining and pivoting stud.

13. Device as in claim 1, further comprising a deformable adapter, which may be inserted into said common hosting hole and provided with a longitudinal hole into which the appendix portion of said interdental cleaning brush may be inserted.

14. Device as in claim 1, wherein said bush and said central body are overmoulded and are made of incompatible materials so as not to be weldable to each other during an overmoulding process.

15. The device of claim 1, wherein, the bush is rotatably mounted on the core so that rotation of the bush about the core is required to secure the appendix portion within the hole.

* * * * *